United States Patent [19]

Taylor

[11] 4,183,922

[45] Jan. 15, 1980

[54] O,S-DIALYL O,S-UREIDOPHENYL PHOSPHOROTHIOLATES AND PHOSPHORODITHIOATES

[75] Inventor: Ronald Taylor, Coraopolis, Pa.

[73] Assignee: Rohm and Haas Company, Philadelphia, Pa.

[21] Appl. No.: 857,952

[22] Filed: Dec. 6, 1977

[51] Int. Cl.² .................. A01N 9/36; C07F 9/165
[52] U.S. Cl. ........................... 424/211; 260/938
[58] Field of Search ................. 260/938; 424/211

[56] References Cited

U.S. PATENT DOCUMENTS

| 3,957,924 | 5/1976 | Meyer et al. | 260/938 OR |
| 4,051,239 | 9/1977 | Gutman | 260/938 X |

FOREIGN PATENT DOCUMENTS 2354586  5/1974  Fed. Rep. of Germany ........... 260/938

*Primary Examiner*—Anton H. Sutto
*Attorney, Agent, or Firm*—Susan Borden-Evans

[57] ABSTRACT

This invention relates to novel organophosphorothiolates and phosphorodithioates of the formula

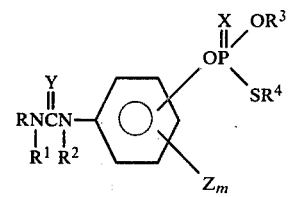

wherein
R is aryl, substituted aryl, arylcarbonyl, or substituted arylcarbonyl;
$R^1$ and $R^2$ are independently hydrogen or alkyl;
$R^3$ and $R^4$ are alkyl;
Z is alkyl, alkoxy, halogen, or trifluoromethyl;
X and Y are independently oxygen or sulfur; and
m is 0 or the integer 1, 2, or 3, to compositions containing them and to methods of using them to control pests.

23 Claims, No Drawings

O,S-DIALYL O,S-UREIDOPHENYL PHOSPHOROTHIOLATES AND PHOSPHORODITHIOATES

This invention relates to novel ureido- and thioureidophenyl phosphorothiolates and phosphorodithioates having pesticidal activity, to composition containing them, and to methods of using them to control various harmful pests. In addition to possessing outstanding pesticidal activity, compounds of the present invention possess such desirable characteristics as activity against organophosphorous resistant species, residual activity, low toxicity to warm-blooded animals and low phytotoxicity for economically important plant species.

The compounds of the invention have the formula

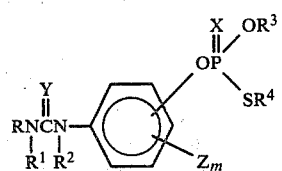

wherein
R is an unsubstituted aryl group, preferably having 6 to 10 carbon atoms, and most preferably a phenyl group, or an aryl group preferably having 6 to 10 carbon atoms and most preferably a phenyl group, substituted with up to three substituents selected from the group consisting of nitro groups, halogen atoms, preferably chlorine atoms; ($C_1$–$C_4$) alkyl groups, preferably ($C_1$–$C_3$) alkyl groups, more preferably methyl groups; ($C_1$–$C_4$) alkoxy groups, preferably ($C_1$–$C_3$)-alkoxy groups, more preferably methoxy groups; ($C_1$–$C_4$)-alkylthio groups, preferably ($C_1$–$C_3$) alkylthio groups, more preferably methylthio groups; trifluoromethyl groups, and cyano groups; or an unsubstituted arylcarbonyl group, preferably having 7 to 11 carbon atoms, and most preferably a phenylcarbonyl group; or an arylcarbonyl group, preferably having 7 to 11 carbon atoms, and most preferably a a phenylcarbonyl group, substituted with up to three substituents selected from the group consisting of nitro groups, halogen atoms, preferably chlorine atoms; ($C_1$–$C_4$)-alkyl groups, more preferably methyl groups; ($C_1$–$C_4$)-alkoxy groups, preferably ($C_1$–$C_3$) alkoxy groups, more preferably methoxy groups; ($C_1$–$C_4$) alkylthio groups, preferably ($C_1$–$C_3$) alkylthio groups, more preferably methylthio groups; cyano groups, and trifluoromethyl groups.

$R^1$ and $R^2$ are independently a hydrogen atom or an alkyl group, preferably having 1 to 4 carbon atoms, more preferably having 1 to 3 carbon atoms, most preferably methyl or ethyl groups; more preferably hydrogen;

$R^3$ is an alkyl group, preferably having 1 to 4 carbon atoms, more preferably having 1 to 3 carbon atoms, most preferably an ethyl group;

$R^4$ is an alkyl group having at least 3 carbon atoms, preferably up to 6 carbon atoms, more preferably having 3 to 5 carbon atoms; most preferably having 3 to 4 carbon atoms;

Z individually, is an alkyl group, preferably having 1 to 4 carbon atoms, more preferably having 1 to 3 carbon atoms, most preferably a methyl group; an alkoxy group, preferably having 1 to 4 carbon atoms, more preferably a methoxy group; a trifluoromethyl group; or a halogen atom, preferably a chlorine atom;

X and Y are independently an oxygen or a sulfur atom; and m is zero or an integer from 1 to 3.

As used in the specification and claims, the terms "alkyl" and "alkoxy" include branched chain as well as straight chain groups. Representative alkyl groups include methyl, ethyl, n-propyl, sec-butyl, isobutyl, pentyl, neopentyl, 2-methylpentyl, n-hexyl and the like. Representative alkoxy groups include methoxy, ethoxy, propoxy, sec-butoxy, pentoxy and the like.

As used in specification and claims, the term "aryl" includes the following representative groups, phenyl, naphthyl, and the like.

The organophosphorothiolates and phosphorodithioates of this invention can exist in any of their isomeric forms in which the ureido or thioureido group of Formula I is attached to the benzene ring in a position which is ortho, meta or para, preferably para, to the point of attachment of the phosphorothiolate or phosphorodithioate group.

The preferred compounds of this invention, i.e., those having especially enhanced acaricidal, insecticidal and nematocidal activity, can be represented by the following formula:

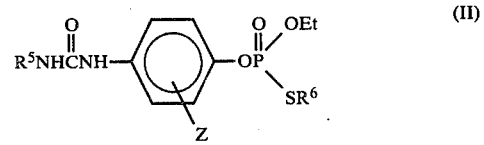

wherein $R^5$ is a phenyl group, optionally substituted with up to two substituents selected from the group consising of methyl, nitro, and chloro; R is either n-propyl or sec-butyl; Z is either hydrogen or methyl; and m is either zero or the integer 1. Typical compounds within the scope of this invention include the following:

O-ethyl O-[2-N'-(4-fluorophenylureido)]phenyl S-propyl phosphorothiolate

O-ethyl O-[3-N'-(3-nitrophenylureido)]phenyl S-propyl phosphorothiolate

O-ethyl O-[4-N'-(2-methylphenylthioureido)]phenyl S-(1-methylpropyl)phosphorodithioate O-ethyl O-[4-N'-(phenylthioureido)]phenyl S-(1-methylpropyl)phosphorodithioate O-[3-N'-(3-chlorophenylureido)-2-methyl]phenyl O-methyl S-(2-methylpropyl)phosphorothiolate O-[3-N'-3,4-dichlorophenylureido)-3-methyl]phenyl O-ethyl S-propyl phosphorodithioate O-[4-N'-methyl-N'-(4-chlorophenylureido)]phenyl O-methyl S-propyl phosphorothiolate O-[4-N-butyl-N'-(4-chlorophenylureido)]phenyl O-ethyl S-propyl phosphorothiolate O-[4-N'-butyl-N'-(4-methoxyphenylureido)]phenyl O-ethyl S-propyl phosphorodithioate O-ethyl O-[4-N'-(3-nitrobenzoylureido)]phenyl S-propyl phosphorothiolate O-[3-N'-(3,5-dichlorobenzoylthioureido)-5-chloro]phenyl O-methyl S-(1-methylpropyl)phosphorothiolate O-ethyl O-[4-N'-(2-butoxy-5-methylthiobenzoylureido)-3-trifluoromethyl]phenyl S-pentyl phosphorothiolate O-ethyl O-[4-N'-(3,4,5-trimethoxybenzoylureido)]phenyl S-propyl phosphorothiolate O-ethyl O-[3-N'-(α-naphthoylureido)]phenyl S-propyl phosphorothiolate O-[2,3,6-trichloro-4-N'-(4-cyanobenzoylureido)]phenyl O-ethyl S-(1-methylpropyl)phosphorothiolate O-[4-N'-(4-butylthio-2-methylbenzoylureido)]phenyl O-ethyl S-(2-methylpropyl)phosphorothiolate S-butyl O-ethyl O-[4-N'-3,4-dimethylbenzoylureido)]phenyl phosphorothiolate O-ethyl O-[2-N'-(4-methoxyphenylureido)]phenyl S-propyl phosphorothiolate O-[4-N'-(4-cyano-2-methylphenylureido)]phenyl O-ethyl S-propyl phosphorothiolate O-[2-N'-(2,4,6-trichlorophenylureido)]phenyl O-ethyl S-(1-methylpropyl)phosphorothiolate O-[4-N'-(2-bromo-4-butylphenylureido)-3,5-dimethyl]phenyl O-ethyl S-(2-methylpropyl)phosphorodithioate O-[4-N'-(4-butylthiophenylureido)-3-butoxy]phenyl O-methyl S-propyl phosphorodithioate O-butyl O-[4-N,N'-dimethyl-N'-(4-methylthiophenylureido)]-phenyl S-(2-methylpentyl)phosphorothiolate O-ethyl O-[2-methoxy-4-N'-(α-naphthylthioureido)]phenyl S-propyl phosphorothiolate O-ethyl O-[2-N'-(4-nitrophenylthioureido)]phenyl S-propyl phosphorothiolate O-[4-N-butyl-N'-(4-butoxyphenylureido)]phenyl O-ethyl S-(1-methylpropyl)phosphorothiolate O-ethyl O-[4-N'-3,5-ditrifluoromethylphenylureido)]phenyl S-(1-methylbutyl)phosphorodithioate The compounds of the present invention can be prepared by a variety of methods well known in the literature. One method involves reacting a phenol of the formula

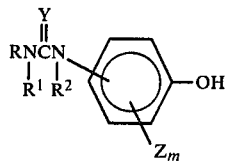   (III)

wherein R, R¹, R², Z, Y and m are as defined above, with an O,S-dialkylphosphorochloridothiolate or phorphorchlorididothioate of the formula

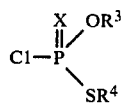   (IV)

wherein R³, R⁴, and X are as defined above.

An acid acceptor such as a tertiary amine or an alkali carbonate or hydroxide can be employed as a scavenger in the preparation. Representative acid acceptors include pyridine, trimethylamine, dimethylaniline, lithium carbonate, sodium hydroxide, potassium hydroxide and the like. Generally, a substantially equimolar ratio of reactants is preferred, but an excess of any of the reactants can be employed. While not required, the reaction is advantageously carried out in the presence of an inert organic solvent such as an ether, aromatic hydrocarbon, halogenated aromatic hydrocarbon, aliphatic ester, aliphatic hydrocarbon, aliphatic ketone, aliphatic nitrile, and the like. Suitable solvents include benzene, xylene, toluene, heptane, tetrahydrofuran, dimethoxyethane, chloroform, chlorobenzene, ethyl acetate, methylethyl ketone, acetone, ethyl ether, acetonitrile and dioxane. The reaction is generally conducted in a temperature range or about 0° to about 100° C. or more, and preferably in the range of about 20° to about 60° C.

Another method of preparing the compounds of this invention involves reacting a metal salt, preferably an alkali metal salt such as a sodium or potassium salt, of a phenol or Formula III, with an O,S-dialkylphosphorochloridothiolate or phosphorochloridothioate of Formula IV. Reaction conditions, including choice of solvents, temperature, and molar ratios correspond to the conditions described above for the reaction of an O,S-dialkylphosphorochloridothiolate or phosphorochlorididothioate with a phenol, except that it is not necessary to employ an acid acceptor in this reaction.

In addition, certain compounds of this invention can be prepared by reacting a metal salt, preferably an alkali salt such as a sodium or potassium salt, of a phenol of Formula III with a phosphorodichloridate or phosphorodichloridothioate of the formula

   (V)

wherein R³ is as defined above. The intermediate phosphorochloridate or phosphorochloridothioate is then reacted directly with a sodium mercaptide of the formula NaSR⁴   (VI)

wherein R⁴ is as defined above, to give the claimed compound defined in Formula I. A typical example of this preparative route is described in Example 25, page 12. Reaction conditions, including choice of solvents, temperature, and molar ratios correspond to the conditions for the two above-described preparative routes, although no acid acceptor need by employed.

All of the starting materials used in the preparation of the compounds of this invention are known compounds or are readily prepared by adaptions of known routes. For example, the phenols of Formula II group are prepared by reacting an appropriate aminophenol with an aryl isocyanate or isothiocyante, and the salts of these phenols by reacting the phenol with a strong base such as sodium hydride, sodium alkoxide, or potassium alkoxide. The O,S-dialkylphosphorochloridothiolate or phosphorochloridodithioates of Formula IV are prepared by reacting an alkylsulfenylchloride with a dialkylchlorophosphite [A. F. Lippman, J. Org. Chem., 30, 3217 (1965)]. The phosphorodithioates are prepared by the method described in Japanese Pat. No. 72/05536.

The following examples are given by way of illustration and are not to be considered as limitations of the present invention. All temperatures are measured in degrees Celsius and all yields in percentage by weight, unless otherwise stated.

EXAMPLE 1

O-[4-N'-(3-Chlorophenylureido)]phenyl O-phenyl S-propyl phosphorothiolate

Sodium hydride (1.69 g of a 57% mineral oil dispersion, 0.04 mol) is added to a dispersion of N-(3-chlorophenyl-N'-4-hydroxyphenyl)urea (7.88 g, 0.03 mol) in 100 ml of dry dimethoxyethane. The mixture is allowed to stir at room temperature for 30 minutes, then a solution of O-ethyl S-propyl phosphorochloridothioate (6.0 g, 0.03 mol) in 40 ml of dimethoxyethane is added dropwise. When the addition is complete, the mixture is stirred at room temperature for two hours, then filtered. The filtrate is evaporated to dryness, then the viscous brown oil residue is dissolved in 200 ml of chloroform, and extracted with two 100 ml portions of water. The organic layer is separated and dried. Evaporation of the solvent in vacuo left 13 g of brown oil which is chromatographed on silica gel to give, in the purest fractions, 2.2 g. of the phosphorothiolate as a viscous oil.

EXAMPLE 2

O-[4-N'-(4-Chlorobenzoylureido)]phenyl O-ethyl S-propyl phosphorothiolate

To a dispersion of N-(4-chlorobenzoyl)-N'-(4-hydroxyphenyl)urea (8.7 g, 0.03 mol) and triethylamine (3.03 g, 0.03 mol) in 150 ml of benzene is added dropwise, O-ethyl S-propyl phosphorochloridothioate (6.07 g, 0.03 mol). The mixture is stirred at 40°-45° for 2½ hours, then at room temperature overnight. The mixture is filtered and the filtrate is extracted with two 100 ml portions of water and dried. Evaporation of the solvent leaves 8.0 g of white solid which is recrystalized from acetone to give 2.12 g of white solid product, mp 130°-1°.

EXAMPLES 3 to 24

In a manner analogous to Examples 1 and 2, the following compounds are likewise prepared.

EXAMPLE 3

O-[4-N'-(4-chlorophenylureido)] phenyl O-ethyl S-(1-methylpropyl)-phosphorothiolate

EXAMPLE 4

O-[4-N'-(4-chlorophenylureido)] phenyl O-ethyl S-(methylethyl)-phosphorothiolate

EXAMPLE 5

O-ethyl O-[4-N'-(3-methylphenylureido)] phenyl S-propyl phosphorothiolate

EXAMPLE 6

O-[4-N'-(4-chlorophenylureido)] phenyl O-ethyl S-propylphosphorothiolate

EXAMPLE 7

O-[4-N'-(4-ethoxyphenylureido)] phenyl O-ethyl S-propylphosphorothiolate

EXAMPLE 8

O-[4-N'-(4-bromophenylureido)] phenyl O-ethyl S-propyl phosphorothiolate

EXAMPLE 9

O-[4-N'-(4-chlorophenylureido)] phenyl O-ethyl S-(2-methylpropyl)-phosphorothiolate

EXAMPLE 10

O-ethyl S-(2-methylpropyl)O-[4-N'-(phenylureido)]phenyl phosphorothiolate

EXAMPLE 11

O-ethyl S-(1-methylpropyl)O-[4-N'-(phenylureido)]phenyl phosphorothiolate

EXAMPLE 12

O-ethyl O-[4-N'-(phenylthioureido)]phenyl S-propylphosphorothiolate

EXAMPLE 13

O-ethyl S-(1-methylpropyl) O-[4-N'-(phenylthioureido)]phenyl phosphorothiolate

EXAMPLE 14

O-ethyl O-[4-N'-(4-nitrophenylureido)]phenyl S-propyl phosphorothiolate

EXAMPLE 15

O-ethyl O-[4-N'-(4-methylphenylureido)]phenyl S-propyl phosphorothiolate

EXAMPLE 16

O-ethyl O-[3-N'-(phenylureido)]phenyl S-propylphosphorothiolate

EXAMPLE 17

O-[3-N'-(4-chlorophenylureido)]phenyl O-ethyl S-propylphosphorothiolate

EXAMPLE 18

O-[4-N'-(3,4-dichlorophenylureido)]phenyl O-ethyl S-propyl phosphorothiolate

EXAMPLE 19

O-[4-N'-(4-chlorophenylureido)-3-methyl]phenyl O-ethyl S-propyl phosphorothiolate

EXAMPLE 20

O-ethyl O-[4-N'-(phenylureido)-3-methyl]phenyl S-propyl phosphorothiolate

EXAMPLE 21

O-ethyl O-[4-N'-(phenylureido)]phenyl S-propyl phosphorothiolate

EXAMPLE 22

O-[4-N'-(2,6-dichlorobenzoylureido)]phenyl O-ethyl S-propyl phosphorothiolate

EXAMPLE 23

O-[4-N'-(benzoylureido)]phenyl O-ethyl S-propyl phosphorothiolate

EXAMPLE 24

O-ethyl O-[4-N'-(2-methylphenylureido)]phenyl S-propyl phosphorothiolate

EXAMPLE 25

O-[4-N'-(4-chlorophenylureido)]phenyl O-ethyl S-propyl phosphorodithioate

Sodium methoxide (1.78 g, 0.033 mol) is added to a dispersion of N-(4-chlorophenyl)-N'-(4-hydroxyphenyl)urea (7.89 g, 0.03 mol) in 200 ml of methanol. After stirring at room temperature for one hour, the mixture is evaporated to dryness, then the residue is slurried with 200 ml of 2-butanone. A solution of ethyl dichlorothiophosphate (5.4 g, 0.03 mol) in 20 ml of 2-butanone is added and the mixture is allowed to stir at room temperature for two hours. It is then filtered, evaporated to dryness, and the residue taken up into 200 ml of benzene and added dropwise to a mixture prepared from 1-propanethiol (2.3 g, 0.03 mol) and sodium hydride (1.4 g of 57%, 0.033 mol) in 320 ml of benzene/acetone (60:40). The mixture is stirred for two hours, filtered, and the filtrate is concentrated in vacuo and the residue is taken up into 300 ml of benzene and extracted with two 100 ml portions of water, and dried. Evaporation of the solvent from the organic layer left 3.31 g of oil residue which solidifies on standing. The solid is slurried with 10 ml of hexane, recovered by filtration, then dried to give 0.67 g of white solid product, mp 101.5°-104.5°.

Table I lists IR and NMR spectral analysis data. The IR data is measured in $cm^{-1}$ and the NMR data is measured in ppm.

TABLE I

SPECTRAL ANALYSIS

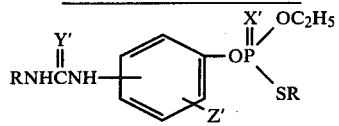

| Example No. | IR(γ,CM$^{-1}$) R | R | X' | Y' | Z' | NH | C=O | NMR(δ, ppm) POC | SCH$_n$ | OCH$_2$ | NH | M.P. °C. |
|---|---|---|---|---|---|---|---|---|---|---|---|---|
| 1 | 4-(3'-Clφ) | C$_3$H$_7$-n | O | O | H | 3390 | 1690 | 1020 | 2.85 | 4.25 | 7.10 7.90 | oil |
| 2 | 4-(4'-ClφC(O)-) | C$_3$H$_7$-n | O | O | H | 3170 | 1650 1680 | 1025 | 2.90 | 4.30 | 10.80 | 130-131 |
| 3 | 4-(4'-Clφ) | C$_4$H$_9$-sec | O | O | H | 3340 | 1702 | 1018 | 3.36 | 4.17 | 7.90 8.17 | 142-143.5 |
| 4 | 4-(4'-Clφ) | C$_3$H$_7$-iso | O | O | H | 3330 | 1700 | 1020 | 3.65 | 4.32 | 7.80 8.19 | 149.5-150.5 |
| 5 | 4-(3'-CH$_3$φ) | C$_3$H$_7$-n | O | O | H | 3330 | 1695 | 1020 | 2.85 | 4.25 | 8.70 | 82-84 |
| 6 | 4-(4'-Clφ) | C$_3$H$_7$-n | O | O | H | 3330 | 1656 | 1031 | 2.84 | 4.25 | 7.70 8.11 | 120-130 |
| 7 | 4-(4'-C$_2$H$_5$Oφ) | C$_3$H$_7$-n | O | O | H | 3280 | 1690 | 1015 | 2.90 | 4.07 | 7.80 | 106-108 |
| 8 | 4-(4'-Brφ) | C$_3$H$_7$-n | O | O | H | 3330 | 1695 | 1015 | 2.90 | 4.30 | 7.80 8.10 | 126-129 |
| 9 | 4-(4'-Clφ) | C$_4$H$_9$-iso | O | O | H | 3330 | 1710 | 1030 | 2.79 | 4.29 | 7.22 7.89 | 102.5-105 |
| 10 | 4-φ | C$_4$H$_9$-iso | O | O | H | 3330 | 1680 | 1020 | 2.80 | 4.30 | 8.10 | oil |
| 11 | 4-φ | C$_4$H$_9$-sec | O | O | H | 3408 | 1721 | 1029 | 3.58 | 4.29 | 8.01 8.13 | oil |
| 12 | 4-φ | C$_3$H$_7$-n | O | S | H | 3230 | — | 1025 | 2.85 | 4.20 | 8.60 | oil |
| 13 | 4-φ | C$_4$H$_9$-sec | O | S | H | 3267 | — | 1027 | 3.41 | 4.29 | 8.13 8.27 | oil |
| 14 | 4-(4'-NO$_2$φ) | C$_3$H$_7$-n | O | O | H | 3280 | 1700 | 1020 | 3.10 | 4.38 | 8.35 | 158-160 |
| 15 | 4-(4'-CH$_3$φ) | C$_3$H$_7$-n | O | O | H | 3370 | 1738 | 1026 | 2.89 | 4.29 | 7.89 7.97 | 104-14 106.5 |
| 16 | 3-φ | C$_3$H$_7$-n | O | O | H | 3330 | 1710 | 1030 | 3.00 | 4.35 | 8.30 | oil |
| 17 | 3-(4'-Clφ) | C$_3$H$_7$-n | O | O | H | 3330 | 1700 | 1025 | 2.90 | 4.25 | 7.80 | 109-112 |
| 18 | 4-(3',4'-Cl$_2$φ) | C$_3$H$_7$-n | O | O | H | 3320 | 1710 | 1014 | 2.94 | 4.32 | 7.6 8.47 | oil |
| 19 | 4-(4'-Clφ) | C$_3$H$_7$-n | O | O | 3-CH$_3$ | 3320 | 1710 | 1031 | 2.84 | 4.25 | 7.85 8.36 | 125-128 |
| 20 | 4-φ | C$_3$H$_7$-n | O | O | 3φ3-CH$_3$ | 3380 | 1695 | 1020 | 2.90 | 4.30 | 8.45 | oil |
| 21 | 4-φ | C$_3$H$_7$-n | O | O | H | 3300 | 1692 | 1021 | 2.88 | 4.29 | 7.89 8.05 | 86.0-87.5 |
| 22 | 4-(2',6'-Cl$_2$φC(O)-) | C$_3$H$_7$-n | O | O | H | 3330 | 1700 | 1030 | 2.80 | 4.20 | 8.60 | 135-137 |
| 23 | 4-φC(O)- | C$_3$H$_7$-n | O | O | H | 3230 | 1650 1680 | 1030 | 2.95 | 4.25 | 10.85 11.00 | 103-106 |
| 24 | 4-(2-CH$_3$φ) | C$_3$H$_7$-n | O | O | H | 3260 | 1660 | 1030 | 2.85 | 4.25 | 8.20 | oil |
| 25 | 4-(4'-Clφ) | C$_3$H$_7$-n | S | O | H | 3320 | 1647 | 1027 | 2.92 | 4.31 | 7.65 | 101.5-104.5 |

The compounds of this invention are useful for the protection of plants and animals, including mammals, from the ravages of harmful and annoying pests and the disease organisms which they may carry. These compounds are particularly effective against nematodes and arthropods (e.g., acarids and insects) in varying stages of development. As arthropodicides, the compounds of this invention are especially effective against the leaf-chewing insects, such as are represented by the order Coleoptera and Lepidoptera. Among the nematodes and arthropods which are effectively controlled by the compounds of the present invention are soil nematodes, e.g., the southern root knot nematode (*Meloidogyne incognita*), the southern armyworm (*Spodoptera eridania*), the sucking insects, e.g., the green peach aphid (*Myzus persicae*), soil-dwelling insects, e.g., the southern corn rootworm (*Diabrotica undecimounctata howardi*), houseflies (*Musca domestica*), mites, e.g., the two-spotted spider mite (*Tetranychus urticae*), and others.

Certain of the compounds of this invention are also active as fungicides, e.g., as phytopathogenic fungicides. Some examples of fungicidal diseases controlled by compounds of this invention are rice blast (*Piricularia oryzae*), grape downy mildew (*Plasmopora viticola*), tomato late blight (*Phytophthora infestans*), and wheat stem rust (*Puccinia graminis*).

Generally, control of pests is achieved in accordance with this invention by application of the compounds of this invention in pesticidally (i.e., acaricidally, insecticidally, nematocidally, fungicidally) effective amounts, either directly to the pests to be controlled or to the loci to be protected from attack by such pests. For example, food, fiber, forage, forest, soil and ornamental crops and stored products thereof would represent plant protection loci. Treatment with the compounds of this invention of mammals and their immediate environs similarly constitute representative loci for protection against various annoying ectoparasitic or endoparasitic Acarina (Acari) and Insecta. Accordingly, compounds of the present invention provide utility as the essential active ingredient of pesticidal compositions suitable for agricultural and sanitary purposes.

The term "control" as employed in the specification and claims of this application is to be construed as any means which adversely affects the existence or growth of a living organism. Such means can comprise a complete killing action, eradication, arresting in growth, repulsion, inhibition, reduction in number, or any combination thereof.

For use as pesticides, the compounds of this invention can be used as solutions, suspensions, or mixtures, in organic solvents or formulations. For example, they can be formulated as wettable powders, emulsifiable concentrates, dusts, granular formulations or flowable emulsifiable concentrates. In such formulations, the compounds of this invention are present at a concentration of about 0.0001 to about 99%, preferably about 1 to about 95%, and are extended with an agronomically acceptable liquid or solid carrier. When desired, suitable surfactants are likewise incorporated. Surfactants commonly used in the art can be found in the John W. McCutcheon, Inc. publication "Detergents and Emulsifiers, Annual."

By "agronomically acceptable carrier" is meant any substance which can be utilized to dissolve, disperse or diffuse the chemical incorporated therein without impairing the effectiveness of the toxic agent and which does no permanent damage to such environment as soil, equipment and agronomic crops.

The compounds of this invention can be taken up on or mixed with a finely particled solid carrier, as for example, clays, inorganic silicates, carbonates, and silicas.

Organic carriers can also be employed. Dust concentrates are commonly made wherein compounds are present in the range of about 20 to about 80%. For ultimate applications, these concentrates are normally extended with additional solid to give an active ingredient content of from 1 to about 20%. Granular formulations are made using a granular or pelletized form of carrier, such as granular clays, vermiculite, charcoal or corn cobs, and may contain the active ingredient in from about 1 to about 25% by weight.

Wettable powder formulations are made by incorporating the compounds of this invention in an inert, finely divided solid carrier along with a surfactant which can be one or more emulsifying, wetting, dispersing, or spreading agents or a blend of these. The compounds are usually present in the range of about 10 to about 80% by weight and surfactants in from about 0.5 to about 10% by weight. Commonly used emulsifying and wetting agents include polyoxyethylated derivatives of alkylphenols, fatty alcohols, fatty acids, alkylamines, alkylarene sulfonates and dialkyl sulfosuccinates. Spreading agents include such materials as glycol mannitan laurate and a condensate of polyglycerol and oleic acid modified with phthalic anhydride. Dispersing agents include such materials as the sodium salt of the copolymer of maleic anhydride and an olefin such as diisobutylene, sodium lignin sulfonate and sodium formaldehydenaphthalene sulfonates.

One convenient method for preparing a solid formulation is to impregnate the compounds of this invention onto the solid carrier by means of a volatile solvent, such as acetone. In this manner, adjuvants, such as activators, adhesives, plant nutrients, synergists and various surfactants can also be incorporated.

Emulsifiable concentrate formulations are prepared by dissolving the compounds of this invention in an agronomically acceptable organic solvent and adding a solvent soluble emulsifying agent. Suitable solvents are chlorinated hydrocarbon, ketone, ester, alcohol and amide classes of organic solvents. Mixtures of solvents are commonly employed. The surfactants useful as emulsifying agents can constitute about 0.5 to about 10% by weight of emulsifiable concentrates and can be anionic, cationic or nonionic in character. The concentration of the active ingredients can vary from about 10 to about 80%, preferably in the range of about 25 to about 50%.

For use as pesticidal agents, these compounds should be applied in an effective amount sufficient to exert the desired pesticidal activity by techniques well known in the art. In certain situations, however, it may be desirable and advantageous to apply the compounds directly onto the loci to be protected or freed of pests without the benefit of any substantial amount of carrier. This is a particularly effective method when the physical nature of the toxicants is such as to permit what is known as "low-volume" application, that is, when the compounds are in liquid form or substantially soluble in higher boiling solvents.

The application rate will, of course, vary depending upon the purposes for such application, the compound being utilized, the frequency of dissemination, and the like.

Many of the above formulations can be utilized on animals for the control of parasites.

For use as arthropodicides, e.g., acaricides and insecticides, dilute sprays can be applied at concentrations of about 0.01 to about 20 pounds of the active ingredients per 100 gallons of spray. They are usually applied at about 0.1 to about 5 pounds per 100 gallons. In more concentrated sprays, the active ingredient is increased by a factor of 2 to 40. With dilute sprays, applications are usually made to the plants until run-off is achieved, whereas with more concentrated or low-volume sprays, the materials are applied as mists.

For use as a nematocide or as a soil insecticide, the compounds can be applied as a dilute liquid preparation or as a solid formulation, preferably a granular formulation, by broadcasting, side-dressing, introduction into the seed furrow, soil incorporation, or seed treatment. The application rate can be from about 1 to about 50 pounds per acre of active ingredient and for economic reasons, preferably from about 1 to about 25 pounds per acre.

For use as a fungicide, the compounds of this invention can be applied as fungicidal sprays by methods commonly employed such as, conventional high-gallonage hydraulic sprays, low-gallonage sprays, ar-blast sprays, aerial sprays and dusts. The dilution and rate of application will depend upon the type of equipment employed, the method of application and diseases to be controlled, but the preferred effective amount is usually about 0.1 lb. to about 50 lbs. per acre of the active ingredient.

As a fungicidal seed protectant, the amount of toxicant coated on the seed is usually at a dosage rate of about 0.1 to about 20 ounces per hundred pounds of seed. As a soil fungicide, the chemical can be incorporated in the soil or applied to the surface usually at a rate of about 0.1 to about 50 lbs. per acre. As a foliar fungicide, the toxicant is usually applied to growing plants at a rate of about 0.25 to about 10 lbs. per acre.

The compounds of this invention can be utilized as the sole pesticidal agents or they can be employed in conjunction with other bactericides, fungicides, herbicides, insecticides, acaricides, and comparable pesticides.

Many variations of this invention are possible without departing from the spirit or scope thereof.

We claim:

1. A compound of the formula:

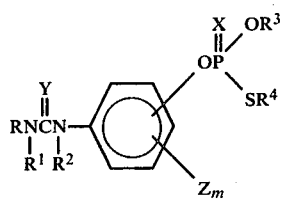

wherein
R is
  (a) an unsubstituted $(C_6-C_{10})$aryl group or a $(C_6-C_{10})$aryl group independently substituted with up to 3 substituents selected from the group consisting of nitro groups, halogen atoms, $(C_1-C_4)$alkyl groups, $(C_1-C_4)$alkoxy groups, $(C_1-C_4)$alkylthio groups, cyano groups and trifluoromethyl groups,
  (b) an unsubstituted $(C_6-C_{10})$aryl carbonyl group or a $(C_6-C_{10})$aryl carbonyl group substituted with up to 3 substituents selected from the group consisting of nitro groups, halogen atoms, $(C_1-C_4)$alkyl groups, $(C_1-C_4)$alkoxy groups, $(C_1-C_4)$alkylthio groups, cyano groups and trifluoromethyl groups;
$R^1$ and $R^2$ are independently a hydrogen atom or a $(C_1-C_4)$alkyl group;
$R^3$ is a $(C_1-C_4)$alkyl group;
$R^4$ is a $(C_3-C_6)$alkyl group;
Z is a $(C_1-C_4)$alkyl group, a $(C_1-C_4)$alkoxy group, a halogen atom, or a trifluoromethyl group;
X and Y are independently an oxygen or sulfur atom; and
m is zero or an integer from 1 to 3.

2. A method of controlling pests which comprises applying directly to the pests or to the loci to be freed of or protected from attack by such pests, a pesticidally effective amount of a compound of claim 1.

3. A compound according to claim 1 wherein R is an unsubstituted phenyl carbonyl or a phenyl carbonyl group substituted with up to 3 substituents selected from the group consisting of nitro groups, halogen atoms, $(C_1-C_3)$alkyl groups, $(C_1-C_3)$alkoxy groups, $(C_1-C_3)$alkylthio groups, cyano groups and trifluoromethyl groups.

4. A compound according to claim 1 wherein R is an unsubstituted phenyl group or a phenyl group substituted with up to three substituents selected from the group consisting of nitro groups, halogen atoms, $(C_1-C_3)$alkyl groups, $(C_1-C_3)$alkoxy groups, $(C_1-C_3)$alkylthio groups, cyano groups and trifluoromethyl groups.

5. A compound according to claim 4 wherein R is unsubstituted phenyl or phenyl substituted with up to two substituents selected from the group consisting of nitro groups, chlorine atoms, methyl groups, ethyl groups, methoxy groups, methylthio groups, cyano groups and trifluoromethyl groups.

6. A compound according to claim 5 wherein
$R^1$ is a hydrogen atom or a $(C_1-C_3)$ alkyl group;
$R^2$ is a hydrogen atom or a $(C_1-C_3)$ alkyl group;
$R^3$ is a $(C_1-C_3)$ alkyl group;
$R^4$ is a $(C_3-C_5)$ alkyl group;
Z is a halogen atom, a $(C_1-C_3)$ alkyl group, a $(C_1-C_3)$ alkoxy group, or a trifluoromethyl group;
X and Y are oxygen atoms; and
m is zero or the integer 1.

7. A compound according to claim 6 wherein
$R^1$ is a hydrogen atom, an ethyl group or a methyl group;
$R^2$ is a hydrogen atom, an ethyl group or a methyl group;
$R^3$ is an ethyl group or a methyl group;
$R^4$ is a $(C_3-C_4)$ alkyl group;
Z is a chlorine atom, a methyl group, a methoxy group, or a trifluoromethyl group.

8. A compound according to claim 7 wherein
$R^1$ is a hydrogen atom; and
$R^2$ is a hydrogen atom.

9. A compound according to claim 8 having the following formula:

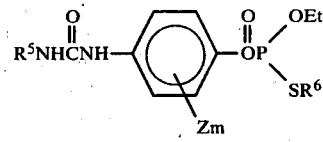

wherein $R^5$ is a phenyl group, optionally substituted with up to two substituents selected from the group consisting of methyl, nitro, and chloro; $R^6$ is either n-propyl or sec-butyl; Z is methyl; and m is either 0 or 1.

10. A compound according to claim 9 having the formula

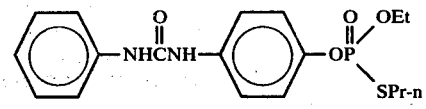

11. A compound according to claim 9 having the formula

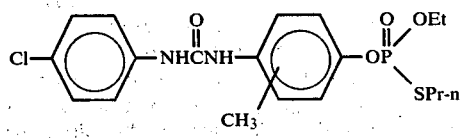

12. A compound according to claim 9 having the formula

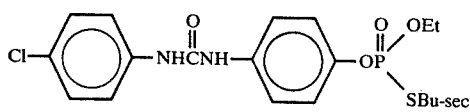

13. A compound according to claim 9 having the formula

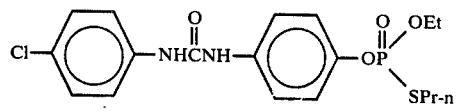

14. A pesticidal composition comprising a compound according to claim 1 and an agronomically acceptable carrier.

15. A pesticidal composition comprising a compound according to claim 9 and an agronomically acceptable carrier.

16. A method of controlling pests which comprises applying directly to the pests or to the loci to be freed of or protected from attack by such pests, a pesticidally effective amount of a composition of claim 15.

17. A method according to claim 16 wherein the pests are arthropods, nematodes or fungi.

18. A method according to claim 17 wherein the pests are nematodes.

19. A method according to claim 17 wherein the pests are phytopathogenic fungi.

20. A method according to claim 17 wherein the pests are arthropods.

21. A method according to claim 20 wherein the arthropods are insects.

22. A method according to claim 21 wherein the insects are leaf chewing insects.

23. A method according to claim 20 wherein the arthropods are acarids.

* * * * *

UNITED STATES PATENT AND TRADEMARK OFFICE
CERTIFICATE OF CORRECTION

PATENT NO. : 4,183,922
DATED : January 15, 1980
INVENTOR(S) : Ronald Taylor

It is certified that error appears in the above-identified patent and that said Letters Patent are hereby corrected as shown below:

In TABLE I bridging columns 7-8:

In the line of the heading beginning "Example", change "IR(y, CM$^{-31}$ 1)" to -- IR(y, CM$^{-1}$) --.

In the line corresponding to Example No. 15 under the last column, "M.P.°C.", change "104-14 106.5" to -- 104-106.5 --.

In the line corresponding to Example No. 20 under the sixth and seventh columns, "Z'" and "NH", respectively change "303-CH$_3$80" (columns merged together) to -- 3-CH$_3$ 3280 - (columns corrected and separated).

Signed and Sealed this

Twenty-eighth Day of October 1980

[SEAL]

Attest:

SIDNEY A. DIAMOND

Attesting Officer

Commissioner of Patents and Trademarks